United States Patent [19]

Shroot et al.

[11] Patent Number: 5,215,520
[45] Date of Patent: Jun. 1, 1993

[54] METHOD FOR DELIVERING AN ACTIVE SUBSTANCE TOPICALLY OR PERCUTANEOUSLY

[75] Inventors: Braham Shroot, Antibes, France; Philip Green, Nyon, Switzerland

[73] Assignee: Centre Internationale de Recherches Dermatologiques Galderma (C.I.R.D. Galderma), Valbonne, France

[21] Appl. No.: 760,982

[22] Filed: Sep. 17, 1991

[51] Int. Cl.$^5$ ............................................. A61N 1/30
[52] U.S. Cl. .................................. 604/20; 128/419 R; 128/803
[58] Field of Search .................. 604/20; 128/799, 803, 128/419 R

[56] References Cited

U.S. PATENT DOCUMENTS

| | | | |
|---|---|---|---|
| 3,964,477 | 6/1976 | Ellis et al. | 604/20 |
| 4,141,359 | 2/1979 | Jacobson et al. | 604/20 |
| 4,301,794 | 11/1981 | Tapper | 604/20 |
| 4,406,658 | 9/1983 | Lattin et al. | 604/20 |
| 4,474,570 | 10/1984 | Ariura et al. | 128/798 |
| 4,764,164 | 8/1988 | Sasaki | 604/20 |
| 4,878,892 | 11/1989 | Sibalis et al. | 604/20 |

FOREIGN PATENT DOCUMENTS 2206493 1/1989 United Kingdom .

OTHER PUBLICATIONS

Glikfeld et al, "A New System for In Vitro Studies of Lontophoresis", Pharmaceutical Research, vol. 5, No. 7, 1988, pp. 443–446.
Golden et al, "Role of Stratum Corneum Lipid Fluidity in Transdermal Drug Flux", Journal of Pharmaceutical Sciences, vol. 76, No. 1, Jan. 1987, pp. 25–28.
Walters, "Penetration Enhancers and Their Use in Transdermal Therapeutic Systems", Penetration Enhancers, Chapter 10, pp. 197–246.

*Primary Examiner*—Lee S. Cohen
*Assistant Examiner*—Jeffrey R. Jastrzab
*Attorney, Agent, or Firm*—Cushman, Darby & Cushman

[57] ABSTRACT

A method for the topical or percutaneous administration of a cosmetic or pharmaceutically active substance involves applying an electric current to an area of the skin, ceasing to apply the electric current to this area of the skin and then applying an active substance to at least a part of this area of the skin in the absence of an electric current being applied thereto.

8 Claims, 2 Drawing Sheets

METHOD FOR DELIVERING AN ACTIVE SUBSTANCE TOPICALLY OR PERCUTANEOUSLY

SCOPE OF THE INVENTION

The present invention relates to a method for delivering a cosmetic and/or pharmaceutically active substance across or into the skin.

The present invention relates more particularly to a new and improved method for attenuating the barrier function of the skin or mucous membrane to the penetration of a topically applied substance.

This method is employed to enhance penetration and, consequently, efficacy of systemic substances or substances having local activity.

The aim was therefore to lower locally the barrier function of the skin to the penetration of active substances. The systemic delivery of a drug by the topical route is particularly beneficial, for it enables a substance to be administered while avoiding its metabolic degradation in the liver or the stomach. Conversely, the horny layer or stratum corneum possesses a considerable barrier against the influx of externally applied substances.

BACKGROUND OF THE INVENTION

It is already known that the barrier function of the skin can be attenuated by employing a penetration enhancer such as dimethylsulphoxide (DMSO), N-methyl-pyrrolidone, dimethylformamide (DMF), oleic acid or N-dodecylazacycloheptanone-2.

However, penetration enhancers may exert their action through interactions with the lipid bilayers within the intercellular spaces of the stratum corneum. Penetration enhancers such as N-dodecylazacycloheptanone-2 and oleic acid disrupt lipid organization and increase lipid fluidity [Golden G. M., Mckie J. E. and Potts R. O., J. Pharm. Sci. 76: 25-28, 1987].

Penetration enhancers may therefore have systemic toxicity or induce local irritation or alterations to the skin. The use of penetration enhancers is described in detail by Barry B. W. in "Percutaneous Absorption", Chapters 31 and 33, pages 531 to 554 and 567 to 593 [Bronaugh R. L. and Maibach H. I., eds. Dekker (New York) 1989] and by Walters K. A. in "Transdermal Drug Delivery—Developmental issues and Research Initiatives", pages 197-246 [Hadgraft J. and Guy R. H., eds., Dekker (New York) 1989].

Iontophoresis has also been known for a long time to enhance the penetration of active substances into the skin.

According to this technique, an electric current is applied to skin at the same time as the active substance.

Iontophoresis may be defined as the use of electrorepulsive and/or electro-osmotic forces to facilitate the transport of a species across the skin. The former force is employed when a charged molecule is repelled across the skin.

The principle of employing an electro-osmotic force is to enable certain non-charged molecules to be pulled along in the electrically induced solvent flow. In this technique, the current is maintained for a prolonged period. The current may be continuous or pulsed.

However, iontophoresis has certain disadvantages. The drug substances may be unstable in the presence of an electric field and moreover, the long duration of application of the electric current may be uncomfortable or traumatizing for the patient.

DESCRIPTION OF THE INVENTION

The present invention has for its object a method for administering topically or percutaneously at least one active substance in which, as a first stage, an electric current is applied to an area of the skin and then, as a second stage, the active substance(s) to be administered is(are) applied to at least one part of the said area of skin.

According to the present invention, a pre-treatment is carried out initially by application of an electric current and, after the electric current has been stopped, the substance intended for skin penetration is then applied.

According to the present invention, it has been discovered that pre-treatment with an electric current decreases the barrier function of the skin and enhances the rate of penetration of the substance subsequently applied to the skin, and this enables percutaneous treatment to be effected.

In the method of the invention, the duration of the two treatment stages may easily be modified. In particular, the duration of application of electric current, which is an uncomfortable and traumatizing stage for the patient, is generally shorter than in iontophoresis.

Moreover, since the substance intended for skin penetration is applied in the absence of electric current, it is not necessary for the substance to be electrically charged. The method according to the invention also avoids electrically associated stability problems.

The electric current pretreatment stage may be carried out with any of the devices used in iontophoresis. These devices are described, for example, in patents GB-A-2 206 493 and U.S. Pat. No. 4,141,359.

Iontophoresis apparatus generally consists of a system having a negative and a positive electrode, separated so that they may be placed on two suitable locations on the skin. The positive and negative electrodes are preferably within two chambers containing an electrolyte solution, the electrodes being in contact with the skin through this solution. The electrodes are preferably separated by an insulating material. The electrolyte is preferably a stable aqueous gel displaying negative thermorheological behavior, so that this formulation is liquid at low temperature and semi-liquid at body temperature. Low temperature is defined as a temperature below 10° C.

Materials which have the ability to form such a gel include, for example, certain ethylene oxide and propylene oxide copolymers. In particular it should be noted that with copolymers of oxyethylene and oxypropylene having 196 units of ethylene oxide and 67 units of propylene oxide, the gels have a viscosity of 0.5 Pa.s at 10° C. and a viscosity of from 4 to 10 Pa.s at 37° C.

The electrolyte is, for example, 0.1 to 0.6M of a salt solution such as NaCl, KCl, $MgSO_4$ or $MgCl_2$. An NaCl solution is preferred.

The current may be supplied by an external source (accumulator, battery, generator).

Two different metal electrodes may also be employed which are placed in contact with the skin or the mucous membrane and connected by a conductor, the metal of one of the electrodes being selected from the group consisting of magnesium, aluminium and zinc, and the metal of the other electrode being selected from the group consisting of silver and copper.

The current may be either continuous or pulsed between 0.05 and 40 KHz with an off/on ratio of 1:1 to 8:1. A continuous current having a density of from 0.01 to 0.5 mA/cm² is preferably employed.

The duration of the first stage of treatment is preferably between 2 minutes and 6 hours. At the end of this treatment it is preferred that the skin is cleaned.

The second stage in which the active substance intended for penetration across the skin is applied, is preferably carried out within 30 minutes and, preferably, immediately after the current has been stopped. The substance intended for skin penetration is applied to the skin either at the site of the positive electrode or that of the negative electrode.

It is preferably formulated in a suitable vehicle which may be an impregnated pad, a gel, cream, ointment, salve, lotion, a suspension with microparticles or nanoparticles or a polymeric patch.

The substance intended for penetration may be lipophilic or hydrophilic, electrically charged or neutral. The substances which may be used include, among others:

steroidal anti-inflammatory agents such as hydrocortisone, methylprednisolone and dexamethasone derivatives;

local anaesthetics such as lidocaine, procaine, cocaine or prilocaine;

anticancerous substances such as methotrexate, cyclophosphamide, bleomycin and doxorubicin;

analgesics and non-steroidal anti-inflammatory agents such as acetylsalicylic acid, mefenamic acid, indomethacin, ibuprofen, bufexamac, N-benzylphenylacetoxy acetamide or its derivatives and unsaturated fatty acid derivatives such as eicosatriynoic acid;

immunoregulators from the cyclosporin family or from the macrolide family such as derivatives of 11,28-dioxa-4-azatricyclo (22.3.1.0.4,9) octacos-18-ene;

antihistamine agents such as promethazine or cinnarizine;

antiviral agents such as idoxuridine, acyclovir, vidarabine and thymine arabinoside;

vitamins, such as vitamins $B_1$, $B_6$ and C;

antibiotics such as penicillin G, ampicillin, streptomycin and tetracycline;

antifungal agents such as miconazole or econazole nitrate and naftifine or terbinafine hydrochlorides;

vasodilators such as histamine, methacholine, nitroglycerine and verapamil;

vasoconstrictors such as noradrenaline, adrenalin and their derivatives;

antihypertensive agents such as clonidine;

vasculoprotective or veinotonic agents such as horse chestnut extract;

anticholinergics such as scopalamine;

anti-adrenergics such as timolol;

metal ions such as Zn, Mg, Au and Cu ions;

sterols;

nucleotides such as cyclic adenosine-5' (mono-, di- or tri-) phosphate (AMP, ADP or ATP), thymidine-5' monophosphate (TMP) and uridine-5' diphosphate (UDP) and oligonucleotides; and peptides and proteins such as insulin, bradykinin, vasopressin, thyrotropin releasing hormone (TRH), and oligopeptids such as Met-Leu-Phe peptide and Thr-Lys-Pro peptide.

The following examples, given by way of illustration and not by way of limitation, when read with reference to the attached diagrams, will enable the invention to be better understood. In these diagrams:

EXAMPLE 1

Preparation of a Highly Ionized Gel

The gel had the following formulation:

| | |
|---|---|
| N-2-hydroxyethylpiperazine-N'-2-ethane sulphonic acid (HEPES) | 0.596 g |
| NaCl | 0.777 g |
| NaOH (1M) in aqueous solution | q.s. to pH 7.4 |
| Copolymer of oxyethylene and oxypropylene containing 196 EO and 67 PO sold by BASF Co. under the trade name "Lutrol 127" | 25.000 g |
| Water | to 100.000 g |

This gel was prepared as follows: NaCl and HEPES were added to water and the mixture stirred until solubilization was complete. The NaOH (1M) solution was then added up pH 7.4 (approximately 1 g of solution was necessary). The solution was cooled to +5° C. and the copolymer added under vigorous stirring. Agitation was maintained until a homogeneous milk-like solution was obtained. The solution was stored overnight at +4° C.

EXAMPLE 2

Comparative Experiments In vitro

Skin penetration experiments using Thr-Lys-Pro peptide were carried out employing the following techniques conducted under comparable conditions:

1) the method of the present invention which has two stages: pre-treatment by an electric current, then application of the substance without electric current;

2) conventional iontophoresis, in which the current and the substance were applied simultaneously;

3) a method for applying the substance alone (without applying electric current) which will hereinafter be described as "passive procedure";

4) a control experiment, skin treatment without applying current, with the gel used as a vehicle in the techniques described above.

a) Diffusion Cell

Figure 4:
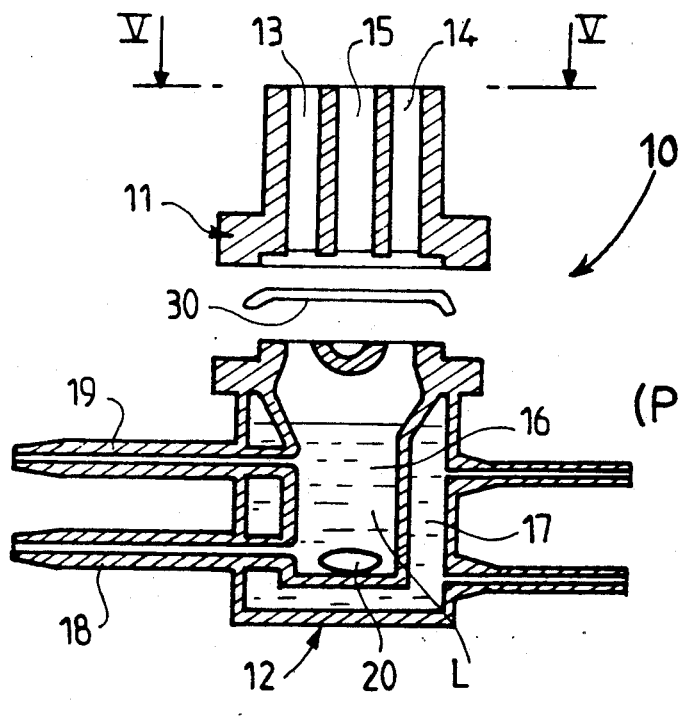
FIGS. 4 and 5 show an in vitro measuring device for "apparent flux" of peptide.
Figure 5:
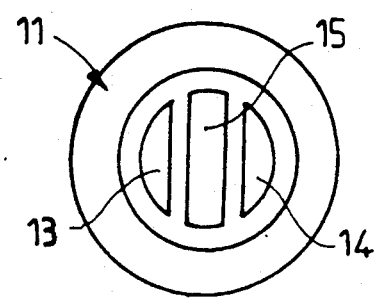

The diffusion cell used is shown in FIGS. 4 and 5 and reported by Glikfeld et al. (Pharm. Res. 5, 443–446, 1988).

This cell (10) consisted of two compartments (11, 12) between which a skin biopsy (30) was then placed. The compartment (11) placed on the stratum corneum side of the skin, or "donor compartment", consisted of three chambers: two chambers capable of containing electrodes (13 and 14) and an intermediate chamber (15). The compartment (12) placed on the dermal side of the skin, or "receptor compartment", is composed of a chamber (16) regulated by a thermostatically controlled water-jacket (17); the chamber (16) contains a feed channel (18) and a receptor liquid phase draw-off channel (19). The chamber (16) contains a magnetic stirrer (20).

The electrodes used were AgCl-coated silver wires, as reported by Thomas, R. C. ("Ion-selective intracellular microelectrodes: How to make and use them", Academic Press, London, 1978) which were inserted in chambers 13 and 14.

b) Solutions Used in Donor Compartment

In the case of conventional iontophoresis, the positively charged peptide was delivered from the anode chamber (13) of the diffusion cell (10). The electrolyte in which the peptide was dissolved and which also surrounded the cathode was a saline gel buffered to pH 7.4; this electrolyte contained a polymeric gel in an aqueous buffer solution containing 25 mM HEPES, 147 mM $Na^+$ and 133 mM $Cl^-$.

The formulation was prepared as described in example 1. Non-radiolabelled peptide at a concentration of 1 $\mu mol/cm^3$ was added to the formulation. The solution obtained was stirred continuously at 5° C. overnight, until a clear liquid was formed. Radiolabelled peptide with a radioactivity of 20 mCi/nmole was added to the gel with stirring, until the mixture had a radiocative concentration of 100 $\mu Ci/cm^3$. The purity of the radiolabelled peptide was determined, prior to use, by high performance liquid phase chromatography.

In the method of the present invention, the gel prepared in example 1 was used in the anode chamber of the donor compartment during the stage when current is passed and, during the stage when the substance is applied in the absence of current, the gel prepared for conventional iontophoresis described above was used.

The gel containing the peptide used for conventional iontophoresis was also used in the "passive" method.

c) Solution Used in the Receptor Compartment

The receptor compartment (12) contained approximately 7 $cm^3$ of HEPES saline solution buffered to pH 7.4 and the solution circulated in the chamber (16) at a flow rate of 12 $cm^3/h$.

d) Skin

Full-thickness abdominal skin, excised and taken immediately after sacrifice, from a female rat (aged 12 to 14 weeks; Nu Ico, Iffa Credo, 69120 Saint-Germain-Sur-Abresle, France) was used.

e) Procedure

First, the dermal side of the skin was perfused with the receptor solution for one hour at a rate of 12 $cm^3/h$. Then 1 $cm^3$ of radiolabelled peptide gel, in the case of application of the substance with current (conventional iontophoresis) or without current (as in the case of the second stage of method of this invention or in passive procedure) or 1 $cm^3$ of gel which contained no peptide (as in the first stage of method of this invention) was introduced into one of the compartments; 1 $cm^3$ of gel which contains no peptide was placed in the other compartment. Ag/AgCl electrodes were placed in chambers 13 and 14 of the donor compartment and, in the case of a current being applied, an electric current density of 0.36 $mA/cm^2$ applied for 6 hours. The current was supplied from a constant current supply comprising 6 independent channels sold by L.A.E.—Laboratoire d'Analyses Electroniques (Nice, France).

For the iontophoresis experiment, the polarity of the current was such that the chamber containing the positively charged peptide was the anode. 6 $cm^3$ samples of receptor solution were collected every 30 minutes and mixed with 12 $cm^3$ of scintillation fluid (sold by Packard Instrument Co. Ltd. under the trade name Picofluor 40). The samples were then counted for radioactivity. The apparent flux of the peptide, as a function of time, was thereby obtained since there is a certain time-lag before receptor solution measurements reflect the establishment of a steady-state flux across the skin.

In the two-stage method of the invention, the gel described in example 1 was placed in the anode chamber of the cell and a current was applied with a current intensity of 0.36 $mA/cm^2$ for 6 hours. Current was stopped and the skin cleaned gently to remove the gel. Some 10 minutes after the current was stopped the gel containing the marked peptide was applied to the anode site and the percutaneous diffusion of the peptide was then monitored for a further 6 hours by measuring the "apparent flux" in the receptor compartment chamber as described above.

In the "passive" method, the gel containing radiolabelled peptide was applied to the skin and percutaneous diffusion was monitored for 12 hours by measuring "apparent flux" in the receptor compartment chamber.

For control purposes, the skin was treated without current for 6 hours with the gel described in example 1 and then treated for a further 6 hours with the gel containing radiolabelled peptide. During the second 6-hour period the "apparent flux" of the peptide across the skin was measured.

Figure 1:
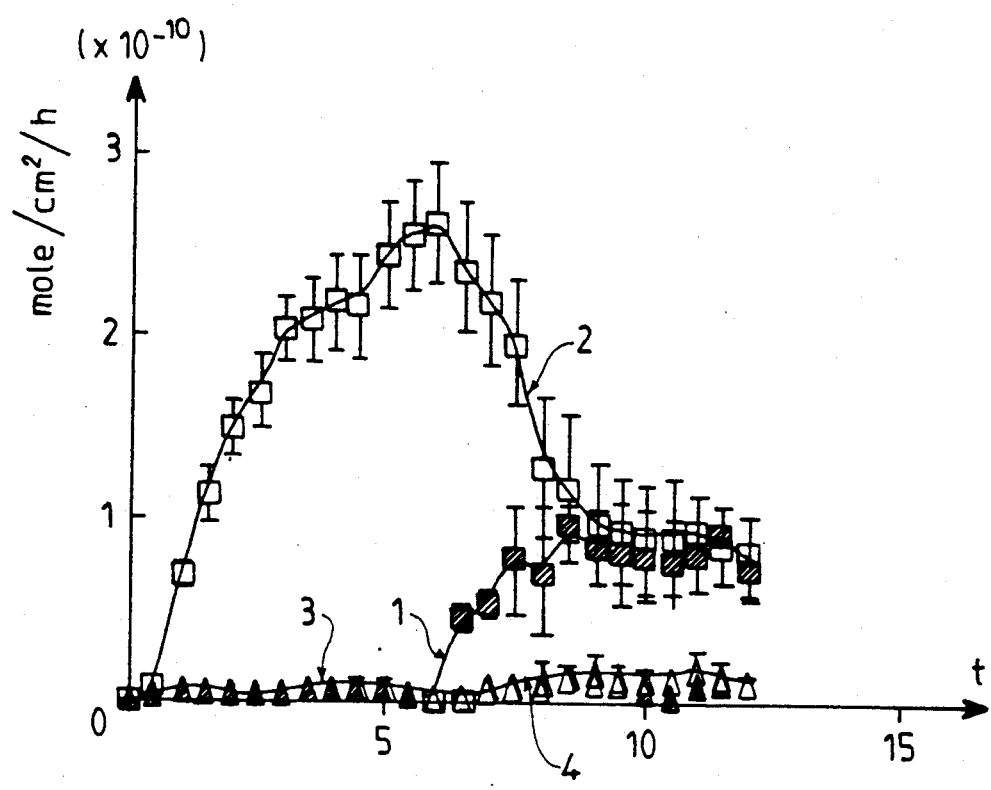
FIG. 1 shows the curves giving the apparent flux of Thr-Lys-Pro peptide in moles/cm²/h measured in vitro.

FIG. 1 shows the various results and gives as ordinates the apparent flux measured in $mol/cm^2/h$ as a function of time. Curve 1 (shaded squares) was obtained by the method of the invention, curve 2 (hollow squares) by conventional iontophoresis for 6 hours, curve 3 (shaded triangles) by the "passive" method and curve 4 (hollow triangles) by the control experiment. Each point of the curve is the average of six measurements; for each point on the curves, the vertical segments correspond to the standard deviation.

It can be seen by comparing curves 1 and 3 that the permeability of the skin to the peptide was greatly increased after 6 hours of pretreatment with electric current and, by comparing curves 1 and 2 that it was analogous to the permeability of the skin obtained after 6 hours of conventional iontophoresis. By comparison of curves 3 and 4 it can be seen that the gel described in example 1 does not have, by itself, any effect on the barrier function of the skin.

EXAMPLE 3

In vivo Experiments

In these experiments, the levels of Thr-Lys-Pro peptide in urine following application of the peptide to the skin were measured.

a) Pharmacokinetic Profile

Prior to the in vivo experiments, a study was carried out to determine whether the levels of peptide in urine were significant. To this end, following a single intravenous injection of Thr-Lys-Pro, its levels in blood and urine were measured. This was carried out by an injection of 0.5 $cm^3$ of an aqueous solution containing 2 $nmol/cm^3$ of non-radiolabelled peptide and 5 $\mu Ci/cm^3$ of radiolabelled peptide via the tail vein of five hairless female rats (198±12 g). The rats had been anaesthetised by an intraperitoneal injection of pentobarbital sodium (40 mg/kg). The rats were left in metabolic cages and blood samples were taken at 10, 15, 30 minutes and 1, 2, 3 and 24 hours following the peptide injection. Blood was removed from the retro-orbital sinus of the eye socket by capillary tube. The samples were weighed into a crucible (ashless paper) and allowed to dry overnight. The blood was then oxidized using a tri-carb oxidizer (model 306 sold by Packard Instrument Co. Inc.) and measured for radioactivity. Urine was collected from the cage after 24 hours and also measured for radioactivity.

Analysis of the blood samples showed that the quantity of peptide in the blood was not detectable. This phenomenon is probably due to the fact that the concentration of peptide in blood decreases very rapidly over time. Indeed, the half-life of a number of peptides in blood has been reported to be around 15 minutes. As such it is conceivable that the flux of peptide is too low to achieve steady state concentrations. In contrast, it was found that the quantity of peptide present in urine 24 hours after the intravenous injection was 63.6±8% of the injected dose. Consequently, the amount of radioactivity within the urine, collected after 24 hours, was used to assess the in vivo percutaneous absorption of Thr-Lys-Pro.

b) Device

Figure 2:
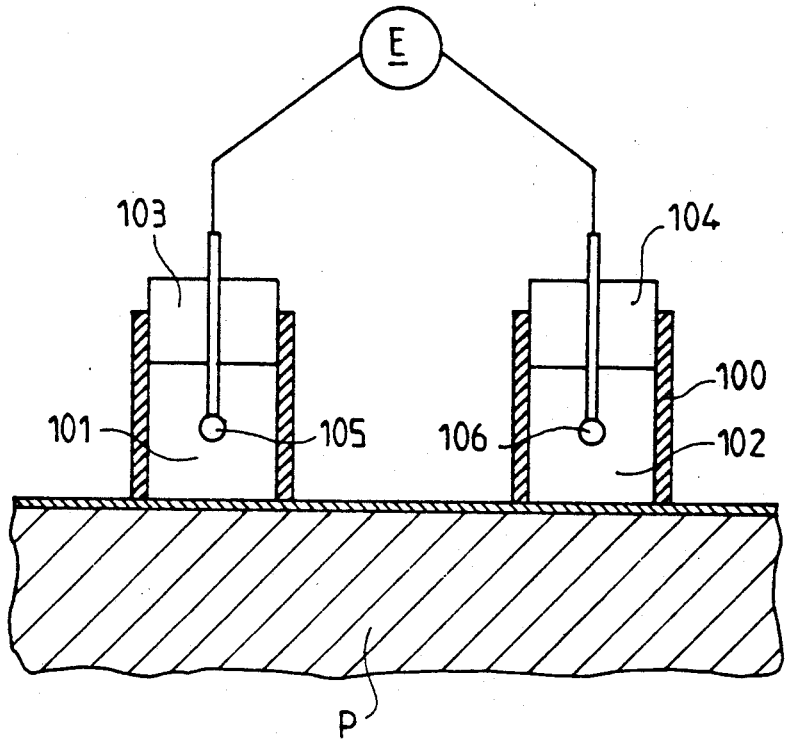
FIG. 2 shows in diagrammatic form an in vivo device for applying a current.

The device used is shown in diagrammatic form in FIG. 2. This device (100) consists of two chambers (101 and 102) the sides of which are surrounded by a plastic cylindrical wall; these chambers are closed at one end by a watertight stopper (103, 104 respectively); the other end is open when it is not in contact with the skin. Electrodes (105, 106) (Ag/AgC1) were tightly fitted to the stoppers (103, 104) and became enclosed within the chambers (101 and 102) when the chambers were closed by replacing the stoppers. The distance between the bottom of the electrode after the stopper has been replaced and the bottom of the chamber is 0.3 cm. The skin surface contact area was 3.80 $cm^2$ and the axes of the chambers were 42 mm apart. The electrodes were connected to a source of electric current (E). To enable the various experiments to be performed, chambers (101 and 102) were fixed to the skin (S) using a cyanoacrylate glue.

c) Experiments

1. For the iontophoresis experiment, the gel containing radiolabelled peptide, as described in example 2, having a temperature of 4° C., was placed in chamber 101 which was fixed to the skin. Similarly, the gel described in example 1 was placed in chamber 102, which was also fixed to the skin. The stoppers (103 and 104) containing the electrodes (105, 106) were then placed in the chambers (101 and 102) so that the electrodes were enclosed within the chambers. A continuous current of 0.36 mA/$cm^2$ was then applied, the chamber containing the peptide gel being the anode.

After 3 hours the electrodes were removed and the skin washed carefully with deionized water, then dried and stripped 5 times with adhesive tape (3M Co., St. Paul, Minn., U.S.A) and the strips discarded. This washing procedure was carried out to remove any trace of radiolabelled peptide which could contaminate the metabolic cages. The rats were then left in their metabolic cages, with free access to food and drink, for 24 hours. The urine passed in the 24-hour period was collected and counted for radioactivity.

2. In the method of the invention, the skin was first subjected to 3 hours of electric current as in conventional iontophoresis, except that chamber 101 contained the gel of example 1 without peptide. After 3 hours the current was stopped, the skin washed and chamber 101 was replaced with an identical chamber, except that it did not contain an electrode, in which gel containing radiolabelled peptide used for iontophoresis was placed. After 3 hours the skin was washed and stripped as in iontophoresis. The rats were then left as described previously in their metabolic cages for 24 hours and urine collected and measured for radioactivity.

3. To perform the "passive" method, gel containing radiolabelled peptide used for iontophoresis was applied for 3 hours in a chamber identical to 101, but which contained no electrode. The rats' skin was then washed and stripped after application as described above. The rats were then left in their metabolic cages for 24 hours and the urine collected in this period measured for radioactivity.

Figure 3:
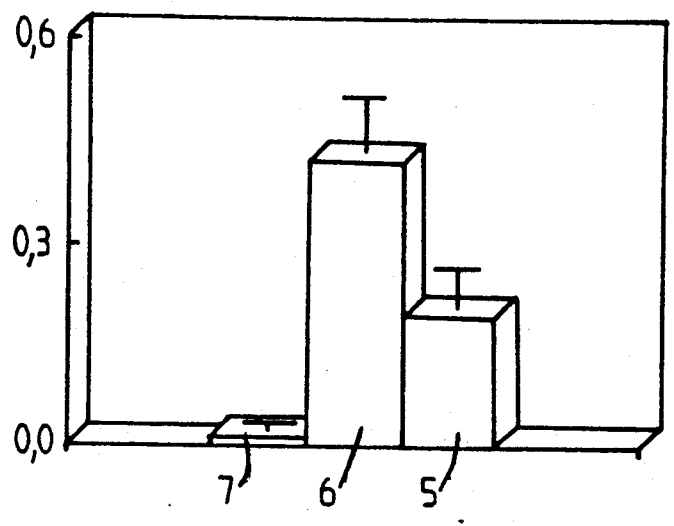
FIG. 3 shows the total quantity of Thr-Lys-Pro peptide measured, in vivo, in urine.

The results are shown in FIG. 3; each datum is the result of 6 measurements (the vertical segments represent the standard deviation); column 5 represents in nmoles (equivalent) the total quantity of peptide in urine obtained by the method of this invention, column 6 the quantity obtained by iontophoresis and column 7 that obtained by the "passive" method.

It can be seen that the method of the present invention enables a greater systemic absorption of peptides than the passive method without application of current.

What we claim is:

1. A method for the topical or percutaneous administration of at least one cosmetic or pharmaceutically active substance comprising, in a first stage, applying to an area of the skin an electric current, ceasing to apply said electric current and, in a second stage, applying an active substance to be administered to at least a part of said area of the skin in the absence of an electric current being applied thereto.

2. The method of claim 1 wherein the step of applying an electric current includes the step of applying a current having a density of from 0.01 to 0.5 mA/$cm^2$.

3. The method of claim 1 wherein the step of applying an electric current includes the step of applying a pulsed current of 0.05 to 40 KHz with an off/on ratio of 1:1 to 8:1.

4. The method of claim 1 wherein the step of applying an electric current in said first stage includes applying said current for a period of time ranging from 2 minutes to 6 hours.

5. The method of claim 1 wherein the step of applying an active substance to said area of the skin in said second stage includes applying said active substance thereto within 30 minutes after ceasing to apply electric current in said first stage.

6. The method of claim 1 wherein said second stage is carried out immediately after ceasing to apply electric current in said first stage.

7. The method of claim 1 which includes cleaning the skin between said first stage and said second stage.

8. A method for the topical or percutaneous administration of at least one cosmetic or pharmaceutically active substance comprising, in a first stage, applying to an area of the skin an electric current, ceasing to apply said electric current and cleaning said area of the skin to which the electric current in said first stage was applied, and in a second stage applying an active substance to be administered to at least a part of said area of the skin in the absence of an electric current being applied thereto.

* * * * *